US011537920B2

(12) United States Patent
Swisher et al.

(10) Patent No.: US 11,537,920 B2
(45) Date of Patent: Dec. 27, 2022

(54) FALSE ALARM DETECTION

(71) Applicant: KONINKLIJKE PHILIPS N.V., Eindhoven (NL)

(72) Inventors: Christine Menking Swisher, San Diego, CA (US); Preetish Rath, Eindhoven (NL); Cornelis Conradus Adrianus Maria Van Zon, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 864 days.

(21) Appl. No.: 16/464,521

(22) PCT Filed: Nov. 21, 2017

(86) PCT No.: PCT/EP2017/079927
§ 371 (c)(1),
(2) Date: May 28, 2019

(87) PCT Pub. No.: WO2018/099767
PCT Pub. Date: Jun. 7, 2018

(65) Prior Publication Data
US 2019/0325332 A1 Oct. 24, 2019

Related U.S. Application Data

(60) Provisional application No. 62/583,529, filed on Nov. 9, 2017, provisional application No. 62/427,220, filed on Nov. 29, 2016.

(51) Int. Cl.
*G06F 15/00* (2006.01)
*G06N 5/04* (2006.01)
(Continued)

(52) U.S. Cl.
CPC ............. *G06N 5/048* (2013.01); *G06N 20/20* (2019.01); *G16H 40/63* (2018.01); *G16H 50/30* (2018.01)

(58) Field of Classification Search
CPC ........ G06N 5/048; G06N 20/20; G16H 40/63; G16H 50/30; G16H 50/70; A61B 5/316;
(Continued)

(56) References Cited

U.S. PATENT DOCUMENTS 8,478,389 B1 * 7/2013 Brockway .............. G16H 50/30
600/509
9,895,111 B2 2/2018 Kudo
(Continued)

FOREIGN PATENT DOCUMENTS

WO    2015171804 A1    11/2015

OTHER PUBLICATIONS

International Search Report and Written Opinion, International Application No. PCT/EP2017/079927, dated Mar. 13, 2018.
(Continued)

*Primary Examiner* — Anh V La

(57) ABSTRACT

Methods and systems for detecting false alarms. Methods and systems described herein may receive data associated with an alarm signal using an interface, extract at least one artifact feature from the received data, and then receive a classification of the alarm signal as a true positive or false positive based on the at least one extracted artifact feature. The classifier may be configured to execute an ensemble of decision trees.

18 Claims, 14 Drawing Sheets

(51) Int. Cl.
*G16H 50/30* (2018.01)
*G16H 40/63* (2018.01)
*G06N 20/20* (2019.01)

(58) Field of Classification Search
CPC ..... A61B 5/363; A61B 5/7221; A61B 5/7242; A61B 5/726
USPC ................ 340/573.1, 539.12, 539.1, 286.07; 706/12; 600/509, 300, 301
See application file for complete search history.

(56) References Cited

U.S. PATENT DOCUMENTS

| | | | | |
|---|---|---|---|---|
| 2008/0208074 | A1* | 8/2008 | Snyder | G16H 50/50 600/545 |
| 2011/0112442 | A1* | 5/2011 | Meger | A61B 5/02055 600/595 |
| 2011/0172504 | A1* | 7/2011 | Wegerich | A61B 5/7264 600/301 |
| 2013/0281799 | A1 | 10/2013 | Burbank et al. | |
| 2015/0364022 | A1 | 12/2015 | Dyell et al. | |
| 2017/0100048 | A1 | 4/2017 | Hu et al. | |
| 2018/0092568 | A1 | 4/2018 | Han | |

OTHER PUBLICATIONS

Wang, X. et al., "A Machine Learning Approach to False Alarm Detection for Critical Arrhythmia Alarms", 2015, IEEE 14th International Conference on Machine Learning and Applications.

Behar, J. et al., "ECG signal quality during arrhythmia and its application to false alarm reduction", Biomedical Engineering, IEEE Transactions on, vol. 60, No. 6, p. 1660, 2013.

Chen, L. et al., "Using Supervised Machine Learning to Classify Real Alerts and Artifact in Online Multisignal Vital Sign Monitoring Data", Jul. 2016, vol. 44, No. 7.

* cited by examiner

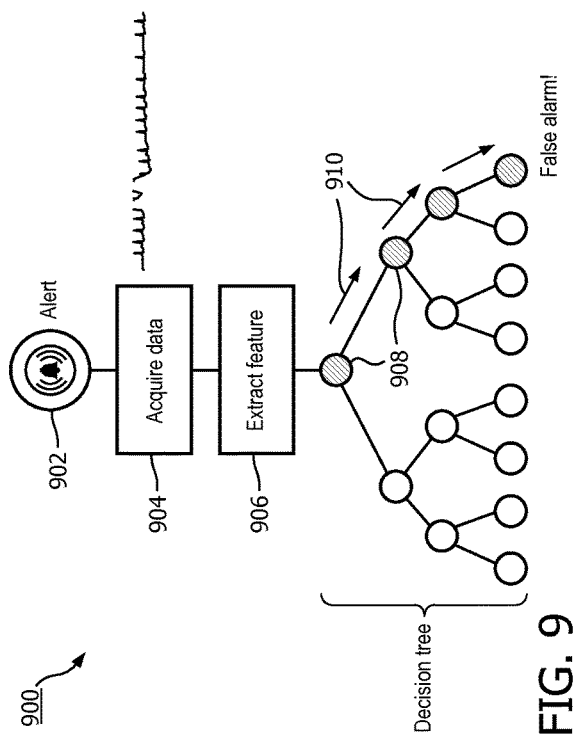
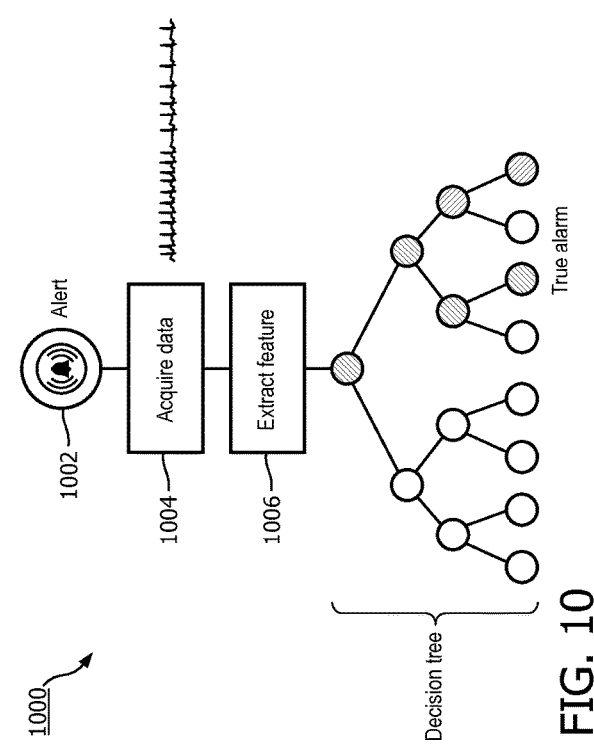

| Artifact | Solution |
|---|---|
| Power line interference (50/60-cycle interference) | Reapply electrodes. Disconnect electrical appliances near patient (one at a time) by pulling wall plugs, to determine faulty grounding. Have engineer check grounding. |
| Muscle artifact | Make sure patient is comfortable. Check that electrodes are applied on flat, non-muscular areas of the torso; reapply electrodes if necessary. |
| Irregular baseline | Reapply electrodes, using proper technique. Move electrodes away from areas with greatest movement during respiration. Apply new electrodes. |
| Baseline wander | Make sure the patient is comfortable. Reapply electrodes. Check that patient cable is not pulling on electrodes. Move electrodes away from areas with greatest movement during respiration. |
| Poor electrode contact | Change all electrodes, using good skin prep. Replace cables. |

FALSE ALARM DETECTION

CROSS-REFERENCE TO PRIOR APPLICATIONS

This application is the U.S. National Phase application under 35 U.S.C. § 371 of International Application No. PCT/EP2017/079927, filed on 21 Nov. 2017, which claims the benefit of U.S. Provisional Patent Applications 62/583,529, filed on 9 Nov. 2017 and 62/427,220, filed on 29 Nov. 2016. These applications are hereby incorporated by reference herein.

TECHNICAL FIELD

Embodiments described herein generally relate to systems and methods for analyzing data associated with alarms and, more particularly but not exclusively, to systems and methods for analyzing data to detect false alarms.

BACKGROUND

Healthcare institutions such as hospitals or the like operate several types of devices to monitor their patients' health. If a device detects a potential anomaly or a cause for concern, the device may issue an alarm. Medical personnel may then perform any required steps to treat the patient.

However, medical devices execute various algorithms that have high sensitivity. This can result in up to hundreds of alarms per patient per day, particularly in clinical units such as the ICU and ED.

Many of these alarms turn out to be clinically irrelevant or are false alarms. In fact, a study at the University of California, San Francisco reported that 2.5 million alarms are triggered in just one month, almost 89% of which are false.

These false alarms result in reduced patient safety and staff satisfaction. Specifically, the flood of alarms may lead clinicians to become desensitized, overwhelmed, or immune to the sound of an alarm. Clinicians may, for example, turn down the alarm volume, turn off the alarm, adjust the device settings, or even completely ignore active alarms. Clinicians may take these actions even if the alarms are true positives that correspond to clinically significant, and possibly life-threatening events.

These actions can have serious or fatal consequences. Therefore, false alarms actually reduce patient safety and are considered a technology-related health hazard.

At the very least, constant alerts cause stress for patients and clinicians. The constant barrage of sound may cause sleep loss and delirium. Additionally, the overabundance of alarms also stresses the healthcare institution by causing constant interruptions in workflow.

A need exists, therefore, for systems and methods for at least detecting false alarms.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

In one aspect, embodiments relate to a method for detecting false alarms. The method includes receiving data associated with an alarm signal using an interface; extracting, using a feature extraction module, at least one artifact feature from the received data; and receiving, using a classifier, a classification of the alarm signal as a true positive or false positive based on the at least one extracted artifact feature.

In some embodiments, the classifier is an ensemble tree classifier executing a plurality of ensemble trees.

In some embodiments, the method further includes assigning a score to the at least one extracted artifact feature using a scoring module upon receiving a classification of a false positive. In some embodiments, assigning the score includes identifying all nodes of each ensemble tree that contribute to the classification of a false positive. In some embodiments, the method further includes summing the scores for all features from each tree, and identifying at least one feature with a score exceeding a threshold.

In some embodiments, the at least one artifact feature extracted is selected from the group consisting of step size, standard deviation of high frequency, baseline wandering, alarm load, heart rate, electrosurgical equipment artifact, motion artifact, respiration artifact, EMG signal, flat line, kurtosis, skewness, and relative power of baseline.

In some embodiments, the method further includes suppressing the alarm signal upon receiving a classification of a false positive.

In some embodiments, the received data is related to a patient and received from a patient monitoring device. In some embodiments, the received data includes EKG data. In some embodiments, the method further includes outputting, using the interface, a report summarizing a classification of at least one alarm signal. In some embodiments, outputting the report includes outputting at least one reason for the classification of the at least one alarm signal.

According to another aspect, embodiments relate to a system for detecting false alarms. The system includes an interface configured to receive data associated with an alarm signal; a memory; a processor executing instructions stored on the memory to provide: a feature extraction module configured to extract at least one artifact feature from the received data, and a classifier configured to provide a classification of the alarm signal as a true positive or false positive based on the at least one extracted artifact feature.

In some embodiments, the classifier is an ensemble tree classifier executing a plurality of ensemble trees.

In some embodiments, the system further includes a scoring module configured to assign a score to the at least one extracted artifact feature upon receiving a classification of a false positive. In some embodiments, the scoring module assigns the score by identifying all nodes of each ensemble tree that contribute to the classification of a false positive. In some embodiments, the classifier is configured to sum the scores for all features from each tree, and identify at least one feature with a score exceeding a threshold.

In some embodiments, the at least one artifact feature extracted is selected from the group consisting of step size, standard deviation of high frequency, baseline wandering, alarm load, heart rate, electrosurgical equipment artifact, motion artifact, respiration artifact, EMG signal, flat line, kurtosis, skewness, and relative power of baseline.

In some embodiments, the processor is further configured to suppress the alarm signal upon receiving a classification of a false positive.

In some embodiments, the received data is related to a patient.

According to yet another aspect, embodiments relate to a computer readable medium containing computer-executable instructions for detecting false alarms. The medium includes computer-executable instructions for receiving data associated with an alarm signal using an interface; computer-executable instructions for extracting, using a feature extraction module, at least one artifact feature from the received data; and computer-executable instructions for receiving, using a classifier, a classification of the alarm signal as a true positive or false positive based on the at least one extracted artifact feature.

BRIEF DESCRIPTION OF DRAWINGS

Non-limiting and non-exhaustive embodiments of the invention are described with reference to the following figures, wherein like reference numerals refer to like parts throughout the various views unless otherwise specified.

FIG. 9 illustrates the traversal of a decision tree in accordance with one embodiment;

FIG. 10 illustrates the traversal of a decision tree in accordance with another embodiment;

FIG. 13 illustrates a table showing various artifacts and artifact solutions in accordance with one embodiment;

DETAILED DESCRIPTION

Figure 1:
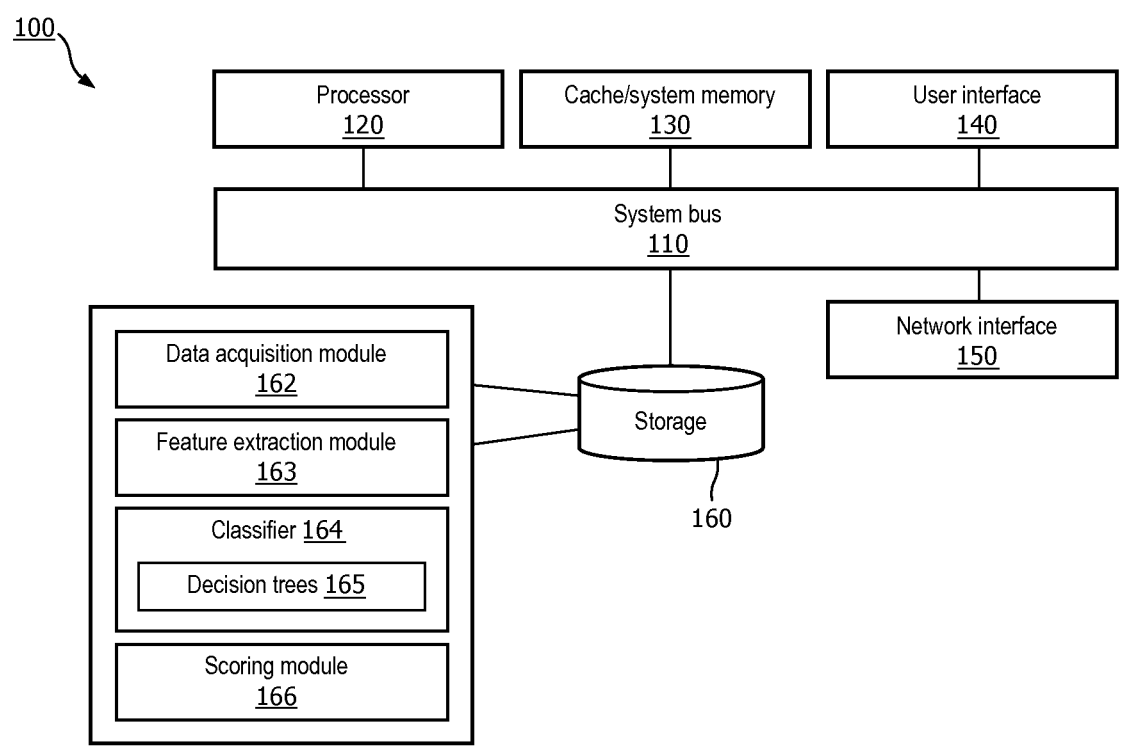
FIG. 1 illustrates a system for detecting false alarms in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques, and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

Features of various embodiments of the systems and methods described herein disclose novel techniques to identify and report statistics on features from signals that indicate preventable, non-physiological events that ultimately lead to false alarms. Possible causes for false alarms may include, for example, motion artifacts, patient discomfort, faulty cables, leads coming from the patient, poor electrode placement, and high gain settings. The systems and methods described herein not only detect false alarms and their corresponding root cause(s), but also suggest actions to prevent or at least reduce the root cause(s). Specifically, features of various embodiments described herein use a reverse mapping approach on a trained ensemble tree classifier to identify the root cause(s) of false alarms.

FIG. 1 illustrates a system 100 for detecting false alarms in accordance with one embodiment. The system 100 includes a processor 120, memory 130, a user interface 140, a network interface 150, and storage 160 interconnected via one or more system buses 110. It will be understood that FIG. 1 constitutes, in some respects, an abstraction and that the actual organization of the system 100 and the components thereof may differ from what is illustrated.

The processor 120 may be any hardware device capable of executing instructions stored on memory 130, on storage 160, or otherwise capable of processing data. As such, the processor 120 may include a microprocessor, field programmable gate array (FPGA), application-specific integrated circuit (ASIC), or other similar devices.

The memory 130 may include various memories such as, for example L1, L2, or L3 cache or system memory. As such, the memory 130 may include static random access memory (SRAM), dynamic RAM (DRAM), flash memory, read only memory (ROM), or other similar memory devices and configurations.

The user interface 140 may include one or more devices for enabling communication with a user. For example, the user interface 140 may include a display, a mouse, and a keyboard for receiving user commands. In some embodiments, the user interface 140 may include a command line interface or graphical user interface that may be presented to a remote terminal via the network interface 150. The user interface 140 may execute on a user device such as a PC, laptop, tablet, mobile device, or the like.

The network interface 150 may include one or more devices for enabling communication with other hardware devices. For example, the network interface 150 may include a network interface card (NIC) configured to communicate according to the Ethernet protocol. Additionally, the network interface 150 may implement a TCP/IP stack for communication according to the TCP/IP protocols. Various alternative or additional hardware or configurations for the network interface 150 will be apparent.

The network interface 150 may be in operable communication with one or more medical devices, for example, patient monitoring devices. These patient monitoring devices may gather data relating to a patient in at least substantially real time and communicate the patient data to the system 100.

The storage 160 may include one or more machine-readable storage media such as read-only memory (ROM), random-access memory (RAM), magnetic disk storage media, optical storage media, flash-memory devices, or similar storage media. In various embodiments, the storage 160 may store instructions for execution by the processor 120 or data upon which the processor 120 may operate.

For example, the storage 160 may include a data acquisition module 162, a feature extraction module 163, a classifier 164 executing a plurality of decision tress 165, and a scoring module 166. The processor 120 may execute instructions stored on the memory 130 to provide each of these components to perform the various features of embodiments described herein. It is noted, however, that the tasks carried out by the various modules are processing functions and, as such, the various modules may be configured with or otherwise as part of the processor 120.

Figure 2:
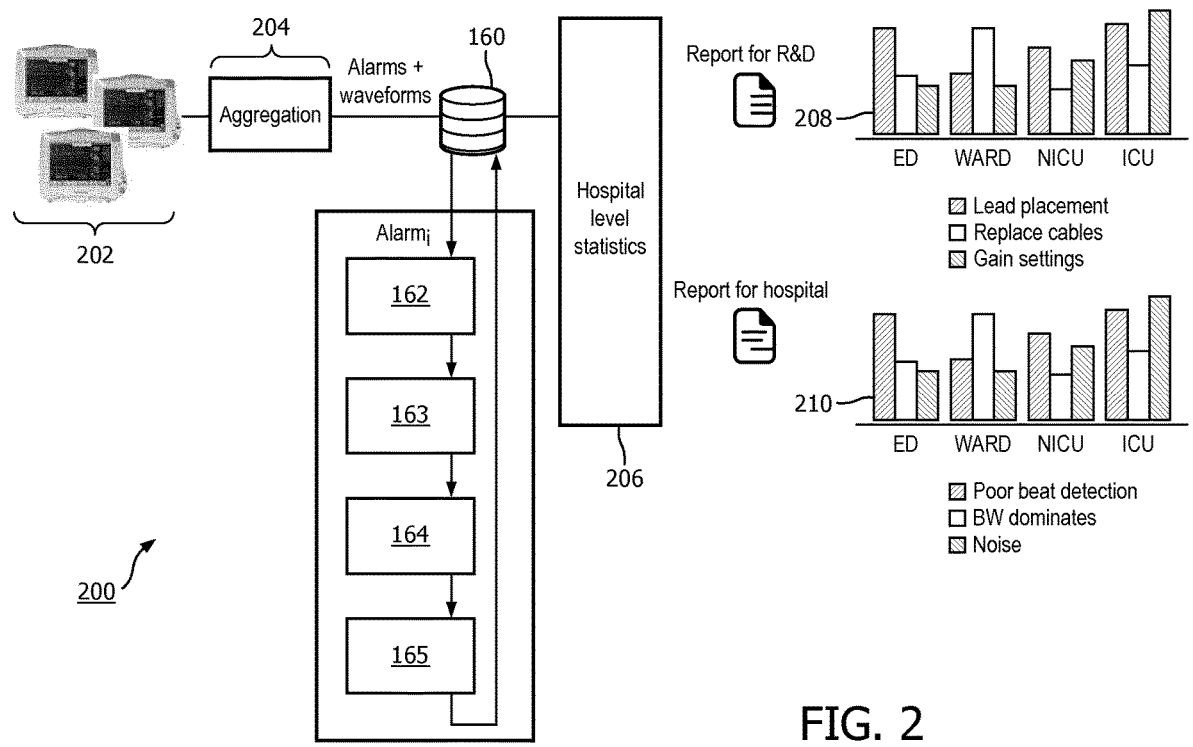
FIG. 2 illustrates an exemplary workflow of the components of FIG. 1 in accordance with one embodiment.

FIG. 2 illustrates an exemplary workflow 200 of the various components of FIG. 1 in accordance with one embodiment. First, various patient monitoring devices 202 may gather data regarding a particular patient. These patient monitoring devices may be configured to gather patient data such as heart rate, temperature, $SpO_2$, EKG data, EMG data, vital sign data, or the like. The types of data considered (as well as the types of devices used to gather the data) may vary as long as features of various embodiments described herein can be accomplished.

One or more displays 204 may present the gathered data in an easy-to-read format. For example the displays 204 may present the data graphically as a wave form. As seen in FIG. 2, the captured data and alarm instances (e.g., when an alarm was generated) may be communicated to the various modules of the storage 160 of FIG. 1.

First, the data acquisition module 162 may aggregate all data through, for example, central stations or an aggregation module 204 and acquire a snapshot of the data. In some embodiments, the data acquisition module 162 may extract a waveform segment corresponding to a certain aspect of a patient's health. For example, this waveform segment may include one or more snapshots of a patient's EKG and/or EMG signal.

The aggregated data may be communicated to the feature extraction module 163. The features extracted may of course vary and may depend on the type of data collected. For example, the features extracted by the feature extraction module 163 may include any one or more of the following:

Step size—this refers to the Analog-to-Digital Converter (ADC) resolution. A large step size could result in steps introduced into an EKG or EMG waveform which, in turn, would imply poor gain settings;

Standard Deviation of high frequency—This indicates the deviation of the frequency spectrum from the mean;

Baseline Wandering—This feature gives an estimate of the wandering of the signal from its baseline;

Alarm load—This feature indicates whether an alarm of the same type (e.g., asystole/V-fib/ . . . ) was triggered within a predetermined time period (e.g., one hour) of the previous alarm;

Heart rate—Calculates the heart rate of the patient;

Electrosurgical equipment artifact—Indicates the presence of high frequency disturbance in an EKG waveform.

This disturbance may be caused by electrosurgical equipment within the proximity of the patient;

Motion artifact—This refers to disturbance in an EKG waveform cause by patient motion;

Respiration artifact—This indicates disturbance in an EKG baseline due to patient respiration;

Percentage of signal free from EMG signal—This indicates the percentage of frequency content of the signal that is free from high frequency EMG noise;

Flat line—This indicates inactivity in the leads of the signal. This may be due to poor electrode placement and/or leads coming off of the patient;

Kurtosis—This indicates a positive correlation with the performance of beat detection;

Skewness—This indicates a positive correlation with the likelihood of a true alarm; and Relative power of baseline—This gives an indication of the signal content that is dominated by baseline wandering.

The above types of features extracted by the feature extraction module 163 are merely exemplary. It is contemplated that other types of features may be extracted and may depend on the types of data gathered by the various patient monitoring device(s) 202.

Figure 3:
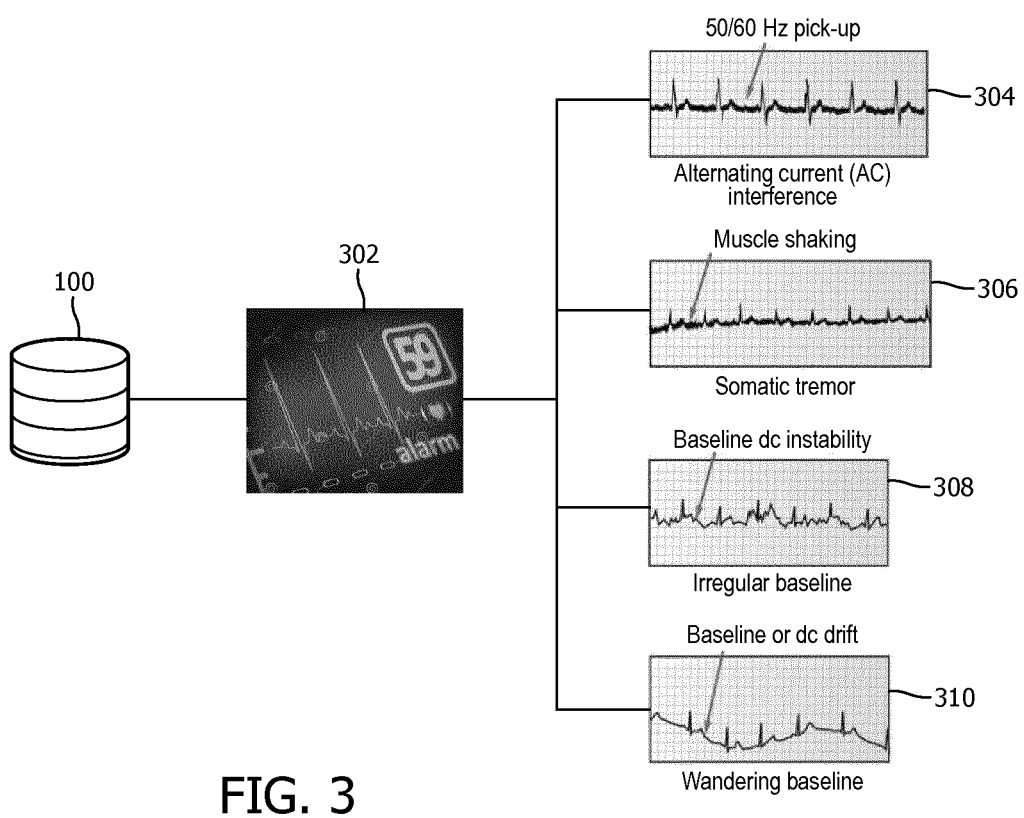
FIG. 3 illustrates the system of FIG. 1 extracting artifact features in accordance with one embodiment.

FIG. 3, for example, illustrates the system 100, extracted data 302, and extracted features 304-310. These features include AC interference 304, somatic tremor 306, irregular baseline 308, and wandering baseline 310.

Figure 4:
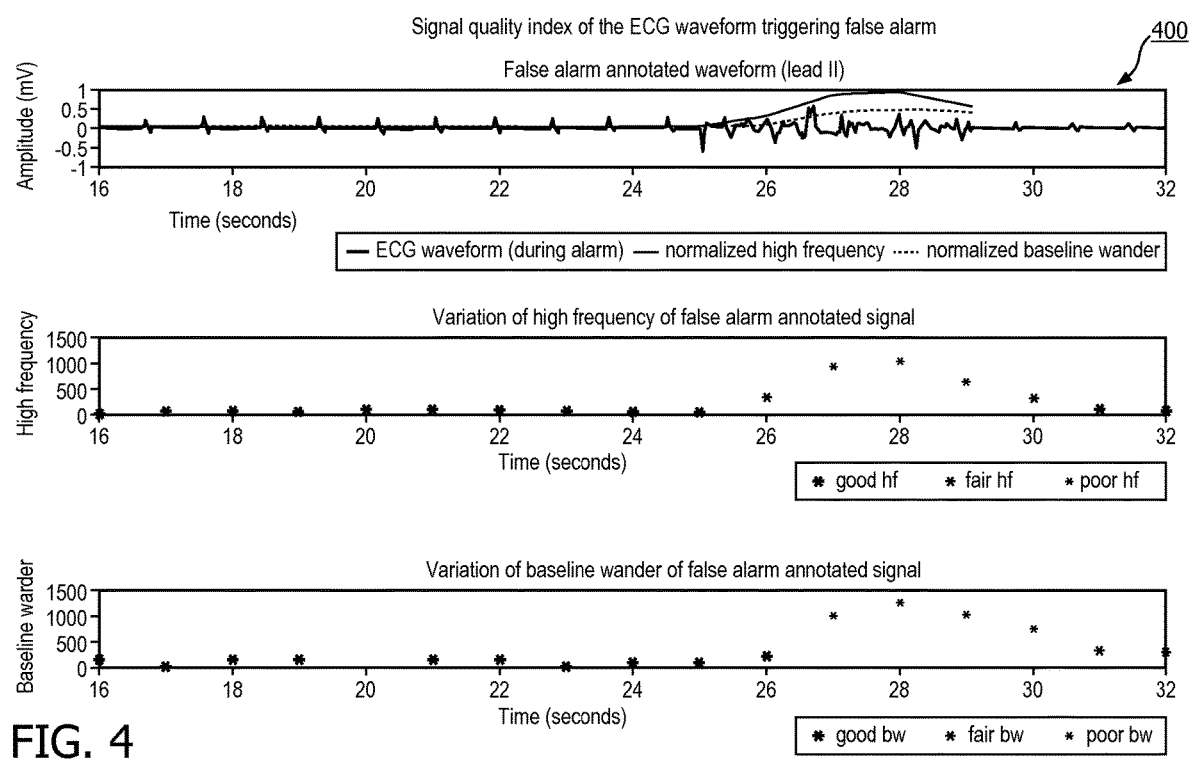
FIG. 4 illustrates a graph showing high frequency and baseline wander artifact features in accordance with one embodiment.
Figure 5:
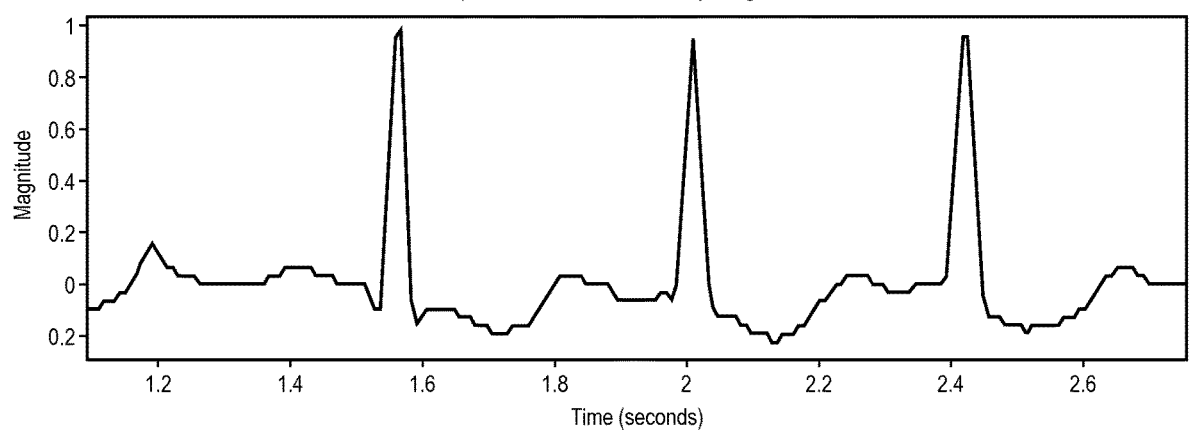
FIG. 5 illustrates a graph showing poor gain selection in accordance with one embodiment.
Figure 6:
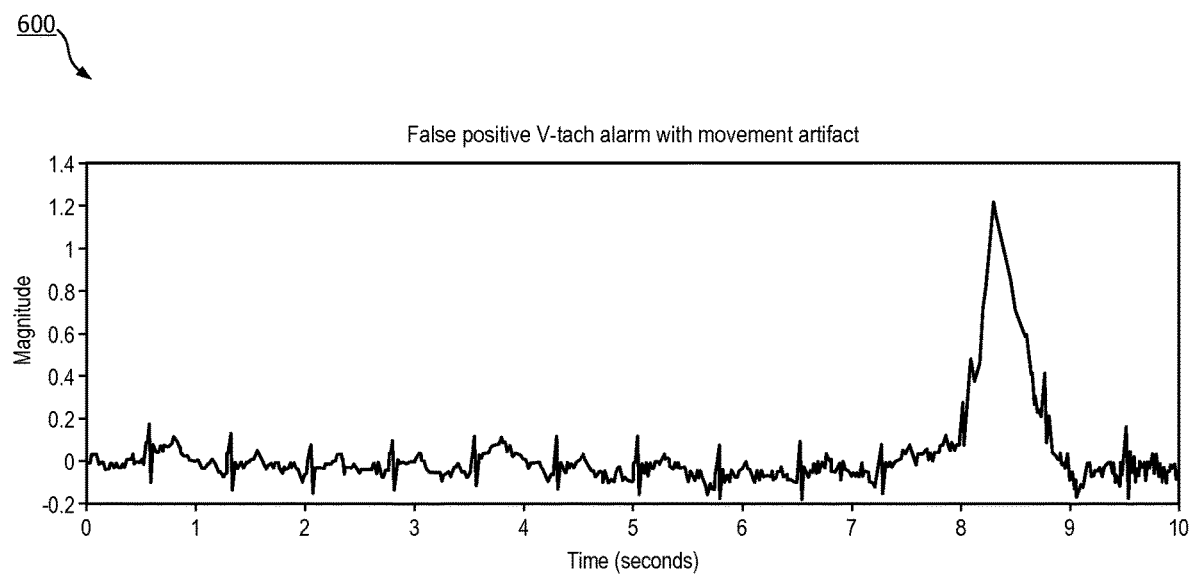
FIG. 6 illustrates a graph showing movement artifact in accordance with one embodiment.

FIGS. 4, 5, and 6 illustrate graphs 400, 500, and 600, respectively, of additional types of exemplary features obtained from EKG data. Specifically, graph 400 shows high frequency and the baseline wander, which provides an estimate of the wandering of the signal from its baseline. Graph 500 illustrates poor gain selection, and graph 600 illustrates movement artifact (e.g., resulting from pain-induced patient movement).

Figure 7:
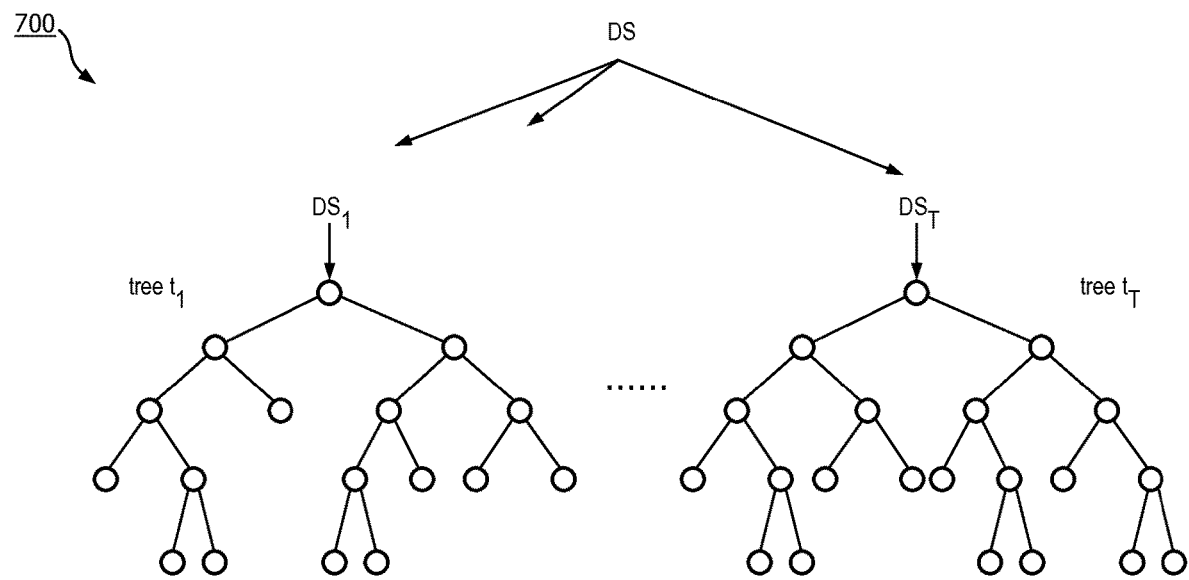
FIG. 7 illustrates an ensemble of a plurality of decision trees executed by the classifier of FIG. 1 in accordance with one embodiment.

Once the appropriate artifact features are extracted, they may be communicated to the classifier 164. The classifier 164 may be previously trained on expert annotated true positive (TP) and false positive (FP) alarms. Specifically, the classifier 164 may be a bagged ensemble tree classifier executing a plurality of decision trees 165. For example, FIG. 7 illustrates an ensemble 700 of a plurality of decision trees $t_1 \ldots t_T$ where T is the number of decision trees in the ensemble 700.

Figure 8:
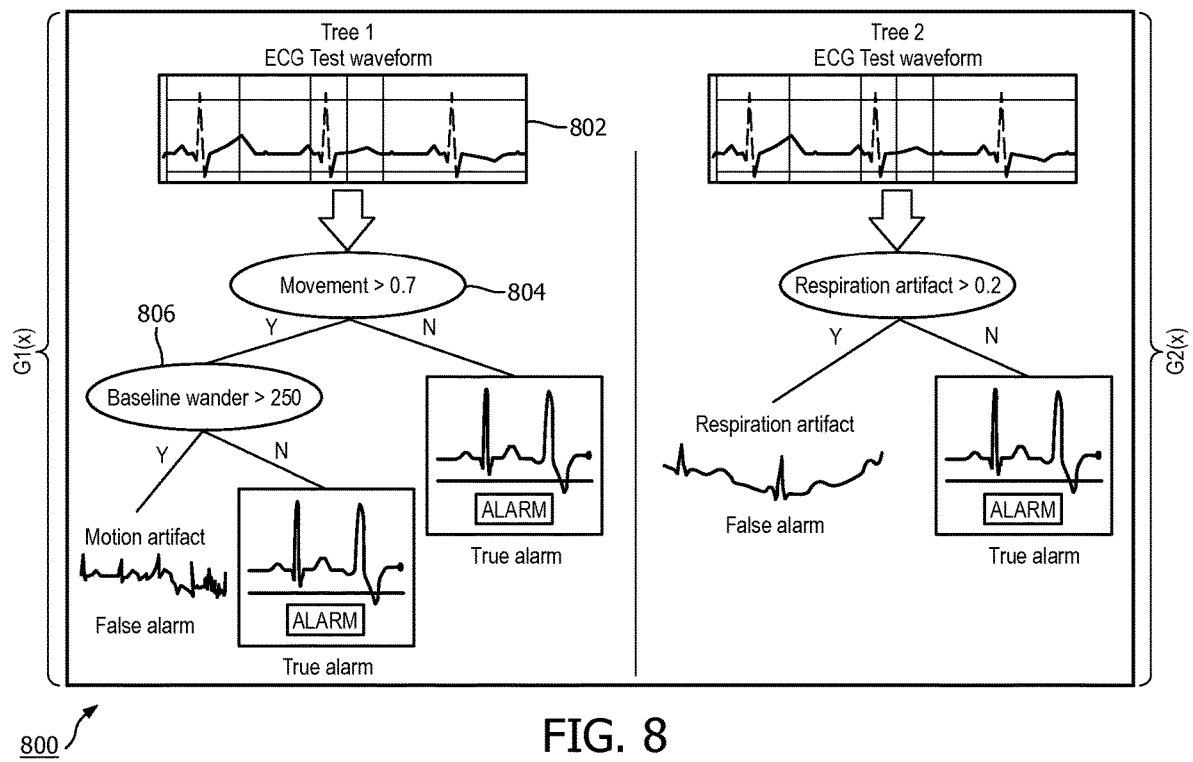
FIG. 8 illustrates exemplary decision trees analyzing artifact features in accordance with one embodiment.

Each decision tree may be built using a random subset of training data. For example, FIG. 8 illustrates exemplary decision trees $G_1(x), G_2(x) \ldots G_m(x)$ where m is the number of trees in the ensemble. Each tree may be built using a feature 802 (an EKG test waveform in FIG. 8), and may include a plurality of nodes 804 that act as a filter or a classifier with respect to some characteristic of the feature 802.

The classifier 164 therefore executes each decision tree 165 to analyze each extracted feature in terms of one or more criteria. As seen in FIG. 8, for example, node 806 of tree $G_1(x)$ asks whether the baseline wander value is greater than some predetermined threshold value. If the baseline wander value is greater than the threshold, tree $G_1(x)$ may determine or at least suggest that this is a false alarm. If the baseline wander value is not greater than the threshold, the tree $G_1(x)$ may determine or at least suggest that this is a true alarm.

FIG. 9 illustrates the traversal of decision tree 900 in accordance with one embodiment. First, an alert 902 (e.g., an alarm signal) is issued by a patient monitoring device. Second, the data acquisition module 162 may obtain a snapshot (e.g., a waveform segment) of the data that caused the alarm signal in step 904. Then, the feature extraction module 163 may extract one or more features from the data in step 906. The extracted feature may relate to a waveform, for example.

The gathered data and extracted feature may then traverse the decision tree 900. The path of the traversal is indicated by the darkened nodes 908 and arrows 910. Depending on the nodes traversed, the decision tree 900 may suggest that this particular alarm signal was a false alarm. Based on the nodes traversed, the classifier 164 may also suggest the cause of the false alarm. For example, the classification of the false alarm by decision tree 900 may be accompanied with a message that this false alarm was caused by poor electrode contact.

FIG. 10 illustrates the traversal of another decision tree 1000. Steps 1002, 1004, and 1006 are similar to steps 902, 904, and 906, respectively, of FIG. 9 and are not repeated here. The data analyzed and/or the extracted feature may be different than those of FIG. 9. As seen in FIG. 10, certain nodes of the decision tree 1000 are traversed that suggest this alarm signal is a true alarm.

The output of all trees may be analyzed by the classifier 164. For example the classifier 164 may note how many trees in an ensemble voted that a particular signal was associated with a false alarm. If the number of trees that suggest an alarm is a false alarm is above a predetermined threshold, the classifier 164 may determine that the signal is a false positive.

The scoring module 166 may then score features for alarms that were classified as false positives. For each tree, the scoring module 166 may identify all relevant nodes that contribute to the alarm being a false positive (e.g., the darkened nodes 908 of FIG. 9).

Figure 11:
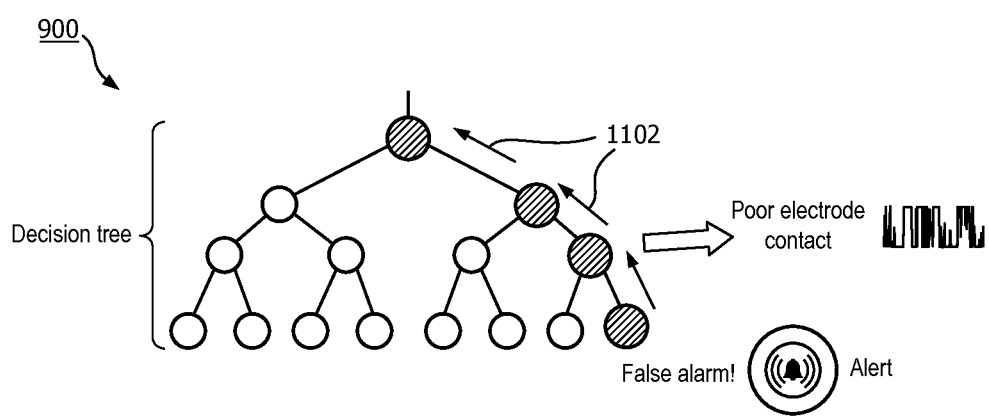
FIG. 11 illustrates the reverse mapping of the decision tree of FIG. 9 in accordance with one embodiment.

FIG. 11 illustrates the decision tree 900 of FIG. 9. As mentioned previously, this decision tree 900 voted that a particular alarm was a false alarm. As seen in FIG. 11, the tree 900 is "reverse mapped" to identify each node that contributed to the alarm being a false positive. This reverse mapping is indicated by arrows 1102.

The scoring module 166 may analyze each tree to obtain the sums of all features for a single alarm. In other words, the scoring module 166 may count how many times a particular feature contributed to a false alarm classification. The classifier 164 may then compare the scores of each feature to a threshold value. If the number of times that a particular feature contributes to a false alarm vote is greater than the threshold value, a clinician may be notified that this feature is a frequent cause of false alarms and that the clinician should take some remedial action.

The reverse mapping can be applied to every alert in a database to identify the most important actions a healthcare institution may take to reduce false positive alarms. Referring back to FIG. 2, the system 100 may then output a report summarizing the gathered statistics 206 regarding the false alarms and their causes. These statistics may be helpful for hospitals (or other types of healthcare institutions), as well as research and development (R&D) departments of various institutions.

Figure 12:
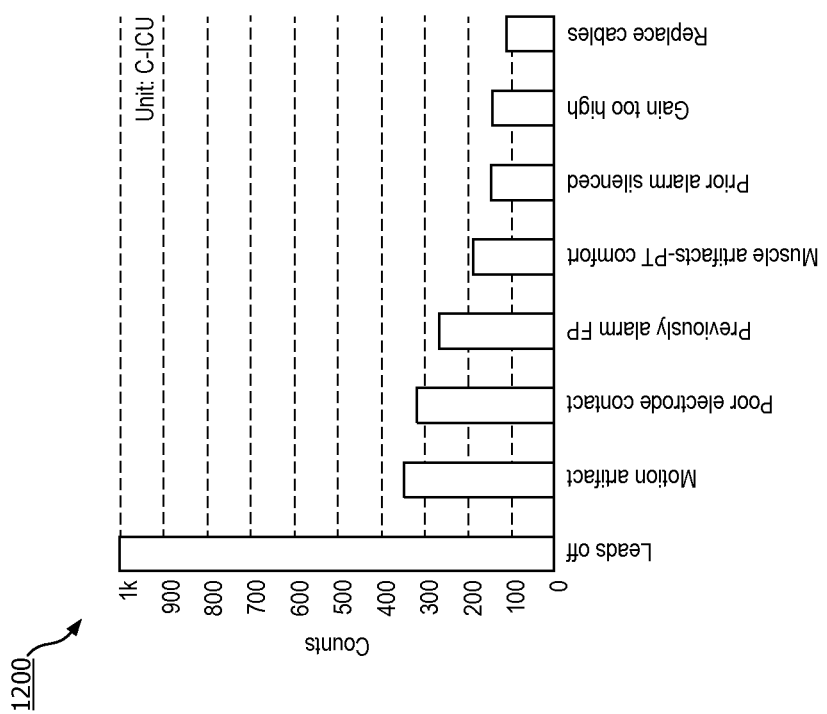
FIG. 12 depicts a bar graph showing counts for frequent features that cause false positives in an ICU unit in accordance with one embodiment.

The reports may summarize the statistics in a variety of ways. For example, FIG. 2 presents bar graphs 208 and 210 showing statistics regarding features that cause false alarms in various units of healthcare institutions. As another example, FIG. 12, depicts a bar graph 1200 showing the counts of the most frequent features that cause false positives in an ICU unit.

The generated report(s) may also include suggestions regarding how to prevent or otherwise mitigate certain feature artifacts from causing false alarms. FIG. 13 illustrates a table 1300 showing various artifacts and possible solutions to prevent each artifact. These types of reports may be presented to a clinician via a user device such as a PC, laptop, tablet, mobile device, or the like.

In addition to outputting data regarding false alarms (and their causes) to clinicians, systems and methods of various embodiments described herein may output this information to R&D departments of various institutions. For example, companies that design or manufacture patient monitoring devices may leverage this type of knowledge to improve their products.

Figure 14:
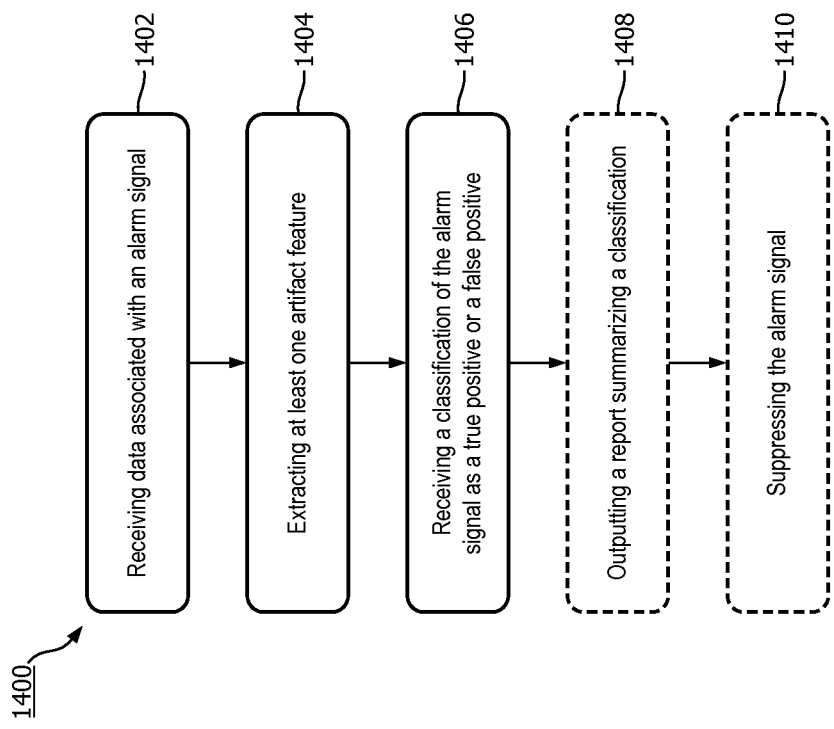
FIG. 14 depicts a flowchart of a method for detecting false alarms in accordance with one embodiment.

FIG. 14 depicts a flowchart 1400 of a method for detecting false alarms in accordance with one embodiment. Step 1402 involves receiving data associated with an alarm signal using an interface. This data may relate to a patient and may be received from one or more patient monitoring devices.

Step 1404 involves extracting, using a feature extraction module, at least one artifact feature from the received data. The feature extraction module may be similar to the feature extraction module 163 of FIG. 1.

The extracted artifact features may include any one or more of, for example, step size, standard deviation of high frequency, baseline wandering, alarm load, EKG data, heart rate, electrosurgical equipment artifact, motion artifact, respiration artifact, EMG signal, flat line, kurtosis, skewness, and relative power of baseline.

Step 1406 involves receiving, using a classifier, a classification of the alarm signal as a true positive or false positive based on the at least one extracted artifact feature. The classifier may be similar to the classifier 164 of FIG. 1 and execute a plurality of decision trees. These decision trees may be similar to the decision trees of FIGS. 7-10, for example, and may each analyze the extracted artifact feature(s) with respect to one or more criteria to classify the alarm as a false positive or a false negative.

Step 1408 involves outputting, using the interface, a report summarizing a classification of at least one alarm signal. This report may help clinicians improve patient care and/or may help R&D departments improve their patient monitoring devices.

Step 1410 involves suppressing the alarm signal upon receiving a classification of a false positive. Although features of the various embodiments described herein are directed towards analyzing classification data to improve patient monitoring devices and/or to improve the patient treatment after alarms are issued, they can also suppress alarms in real time. Accordingly, patients and clinicians are not bothered by excessive alarms.

Figures 15, 16:
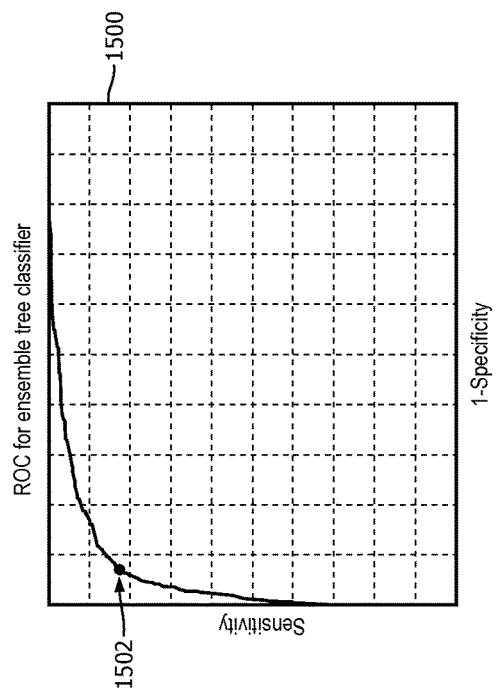
FIG. 15 depicts a receiver operating characteristic (ROC) curve for the ensemble tree classifier of FIG. 1 in accordance with one embodiment.
FIG. 16 illustrates a confusion matrix in accordance with one embodiment.

The accuracy of the system 100 can be improved by increasing the number of trees. For example, FIG. 15 illustrates a receiver operating characteristic (ROC) curve 1500 showing the performance of the ensemble trees classifying the false alarms and the true alarms (e.g., when the number of trees n=90). The ROC curve 1500 plots the specificity, which is also referred to as the true positive rate, vs (1−specificity) where "specificity" is the true negative rate. The area under the curve (AUC) is 0.94.

An ideal ROC curve would have a point with coordinates (0, 1), which would represent classifier performance with no false negatives and no false positives (i.e., perfect classification). However, curve 1500 illustrates favorable results obtained from the trained classifier 164 (e.g., over 6,602 training samples and 1651 test samples). Point 1502, for example, corresponds to a sensitivity rate of 84.12% and a (1−specificity rate) of 93%.

FIG. 16 illustrates a confusion matrix 1600 showing the results of the trained classifier on the 1651 test samples. Box 1602 represents the number of true positives, 612, out of the 1651 test samples. Box 1604 represents the number of false positives, 60, out of the 1651 test samples. Box 1606 represents the number of false negatives, 130, out of the 1651 test samples, and box 1608 represents the number of true negatives, 849. Each box also includes the percentages with respect to the entire test set.

Box 1610 represents the true positive rate or sensitivity. This value is obtained by dividing the sum of the true positives by the number of condition positives. That is:

$$\text{True positive rate} = \frac{\sum \text{true positive}}{\sum \text{condition positives}} = \frac{612}{(612+130)} \times 100 = 82.5\%$$

Box 1610 also represents the false negative rate (i.e., 1−82.5%=17.5%).

Box 1612 represents the false positive rate. This value is obtained by dividing the sum of the false positives by the sum of the condition negatives. That is:

$$\text{False positive rate} = \frac{\sum \text{false positive}}{\sum \text{condition negatives}} = \frac{60}{(60+849)} \times 100 = 6.6\%$$

Box 1612 also represents the true negative rate (i.e., 1−6.6%=93.4%).

Box 1614 represents the positive predicted value. This value is obtained by dividing the sum of the true positives by the sum of predicted condition positives. That is:

$$\text{Positive predicted value} = \frac{\sum \text{true positive}}{\sum pred \text{ condition positives}} = \frac{612}{(612+60)} \times 100 = 91.1\%$$

Box 1614 also represents the false discovery rate (i.e., 1−91.1%=8.9%).

Box 1616 represents the false omission rate. This value is obtained by dividing the sum of the false negatives by the sum of predicted condition negatives. That is:

$$\text{False omission rate} = \frac{\sum \text{false negative}}{\sum pred \text{ condition negatives}} = \frac{130}{(849+130)} \times 100 = 13.3\%$$

Box 1616 also represents the negative predicted value (i.e., 1−13.3%=86.7).

Finally, box 1618 represents the positive likelihood ratio which is equal to the true positive rate divided by the true negative rate. That is:

$$\text{Positive likelihood ratio} = \frac{\text{true positive rate}}{\text{true negative rate}} = \frac{82.5}{93.4} \times 100 = 88\%$$

Box 1618 also represents the negative likelihood ratio (i.e., 1−88%~12%).

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A method for detecting false alarms, the method comprising:
   receiving from a patient monitoring device, using an interface, patient data associated with an alarm signal issued by the patient monitoring device;
   extracting, using a feature extraction module, at least one artifact feature from the received patient data;
   providing, using a classifier, a classification of the alarm signal as a true positive or false positive based on the at least one extracted artifact feature; and
   assigning a score to the at least one artifact feature indicating a contribution of the at least one artifact feature to the false alarm upon classifying the alarm signal as a false positive.

2. The method of claim 1 wherein the classifier is an ensemble tree classifier executing a plurality of ensemble trees.

3. The method of claim 1, wherein assigning the score includes identifying all nodes of each ensemble tree that contribute to the classification of a false positive.

4. The method of claim 3 further comprising summing the scores for all features from each tree, and identifying at least one feature with a score exceeding a threshold.

5. The method of claim 1 wherein the at least one artifact feature extracted is selected from the group consisting of step size, standard deviation of high frequency, baseline wandering, alarm load, heart rate, electrosurgical equipment artifact, motion artifact, respiration artifact, EMG signal, flat line, kurtosis, skewness, and relative power of baseline.

6. The method of claim 1 further comprising suppressing the alarm signal upon receiving a classification of a false positive.

7. The method of claim 1, wherein the received patient data includes EKG data.

8. The method of claim 1 further comprising outputting, using the interface, a report summarizing a classification of at least one alarm signal.

9. The method of claim 8 wherein outputting the report includes outputting at least one reason for the classification of the at least one alarm signal.

10. The method of claim 3, wherein identifying all nodes comprises identifying nodes on a path of traversal of an ensemble tree that voted that the alarm signal was a false alarm.

11. The method of claim 1 wherein scores are assigned to the at least one artifact feature for multiple alarm signals.

12. A system for detecting false alarms, the system comprising:
   an interface configured to receive from a patient monitoring device patient data associated with an alarm signal issued by the patient monitoring device;
   a memory;
   a processor executing instructions stored on the memory to provide:
      a feature extraction module configured to extract at least one artifact feature from the received patient data,
      a classifier configured to provide a classification of the alarm signal as a true positive or false positive based on the at least one extracted artifact feature, and
      a scoring module configured to assign a score to the at least one artifact feature indicating a contribution of the at least one artifact feature to the false alarm upon classifying the alarm signal as a false positive.

13. The system of claim 12 wherein the classifier is an ensemble tree classifier executing a plurality of ensemble trees.

14. The system of claim 12 wherein the scoring module assigns the score by identifying all nodes of each ensemble tree that contribute to the classification of a false positive.

15. The system of claim 12 wherein the classifier is configured to sum the scores for all features from each tree, and identify at least one feature with a score exceeding a threshold.

16. The system of claim 12 wherein the at least one artifact feature extracted is selected from the group consisting of step size, standard deviation of high frequency, baseline wandering, alarm load, heart rate, electrosurgical equipment artifact, motion artifact, respiration artifact, EMG signal, flat line, kurtosis, skewness, and relative power of baseline.

17. The system of claim 12 wherein the processor is further configured to suppress the alarm signal upon receiving a classification of a false positive.

18. A non-transitory computer readable medium containing computer-executable instructions for detecting false alarms, the medium comprising:
   computer-executable instructions for receiving from a patient monitoring device, using an interface, patient data associated with an alarm signal;
   computer-executable instructions for extracting, using a feature extraction module, at least one artifact feature from the received patient data;
   computer-executable instructions for providing, using a classifier, a classification of the alarm signal as a true positive or false positive based on the at least one extracted artifact feature; and
   computer-readable instructions for assigning a score to the at least one artifact feature indicating a contribution of the at least one artifact feature to the false alarm upon classifying the alarm signal as a false positive.

* * * * *